US008440626B2

(12) United States Patent
Amberg et al.

(10) Patent No.: US 8,440,626 B2
(45) Date of Patent: May 14, 2013

(54) ANTINEOPLASTIC PEPTIDES

(75) Inventors: Wilhelm Amberg, Friedrichsdorf (DE);
Teresa Barlozzari, Wellesley, MA (US);
Harald Bernard, Bad Durkheim (DE);
Ernst Buschmann, Ludwigshafen (DE);
Andreas Haupt, Schwetzingen (DE);
Hans-Guenther Hege, Neustadt (DE);
Bernd Janssen, Harvard, MA (US);
Andreas Kling, Manneim (DE); Helmut Lietz, Neustadt (DE); Kurt Ritter, Heidelberg (DE); Martina Ullrich, Schrieshaim (DE); Jurgen Weymann, Bad Durkheim (DE); Thomas Zierke, Bohl-Iggelheim (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 0 days.

(21) Appl. No.: 12/869,314

(22) Filed: Aug. 26, 2010

(65) Prior Publication Data
US 2011/0098235 A1 Apr. 28, 2011

Related U.S. Application Data

(60) Continuation of application No. 12/079,980, filed on Mar. 31, 2008, now Pat. No. 7,807,779, which is a division of application No. 11/179,074, filed on Jul. 11, 2005, now Pat. No. 7,368,528, which is a division of application No. 09/757,142, filed on Jan. 9, 2001, now abandoned, which is a continuation of application No. 09/097,184, filed on Jun. 12, 1998, now abandoned, which is a continuation-in-part of application No. PCT/EP96/05518, filed on Dec. 11, 1996.

(60) Provisional application No. 60/059,062, filed on Dec. 15, 1995.

(51) Int. Cl.
*A61K 38/00* (2006.01)
*A61K 38/08* (2006.01)
*A61P 35/00* (2006.01)
*C07K 7/00* (2006.01)

(52) U.S. Cl.
USPC .......................................... 514/19.3; 530/330

(58) Field of Classification Search ................. 514/19.3; 530/330
See application file for complete search history.

(56) References Cited

U.S. PATENT DOCUMENTS

| 4,816,444 | A | 3/1989 | Pettit et al. |
| 5,502,032 | A | 3/1996 | Haupt et al. |
| 5,504,191 | A | 4/1996 | Pettit et al. |
| 5,530,097 | A | 6/1996 | Pettit et al. |
| 5,554,725 | A | 9/1996 | Pettit |
| 5,831,002 | A | 11/1998 | Haupt et al. |
| 5,864,012 | A | 1/1999 | Amberg et al. |
| 5,886,147 | A | 3/1999 | Amberg et al. |
| 5,965,700 | A | 10/1999 | Amberg et al. |
| 6,015,790 | A | 1/2000 | Barlozzari et al. |
| 6,103,698 | A | 8/2000 | Barlozzari et al. |
| 6,143,721 | A | 11/2000 | Janssen et al. |
| 6,248,865 | B1 | 6/2001 | Amberg et al. |
| 6,458,765 | B1 | 10/2002 | Janssen et al. |
| 6,632,795 | B1 | 10/2003 | Barlozzari et al. |
| 7,084,110 | B2 | 8/2006 | Janssen et al. |
| 7,368,528 | B2 | 5/2008 | Amberg et al. |
| 7,807,779 | B2 | 10/2010 | Amberg et al. |
| 2003/0153505 | A1 | 8/2003 | Janssen et al. |

FOREIGN PATENT DOCUMENTS

| DE | 4415997 A1 | 11/1995 |
| EP | 0398558 A1 | 11/1990 |
| EP | 0598129 B1 | 5/1994 |
| WO | 92/02541 A1 | 2/1992 |
| WO | 93/23424 A1 | 11/1993 |
| WO | 95/30690 A1 | 11/1995 |
| WO | 95/30691 A1 | 11/1995 |
| WO | 96/40751 A1 | 12/1996 |
| WO | 96/40752 A1 | 12/1996 |
| WO | 97/17364 A1 | 5/1997 |

OTHER PUBLICATIONS

Voskoglou-Nomikos et al., 2003, Clinical Predictive Value of the in vitro Cell line, Human Xenograft, and Mouse Allograft Preclinical Cancer Models, Clinical Cancer Research, 9: 4227-4239.*
Kingston et al., 2009, Tubulin-Interactive Natural Products as Anticancer Agents, J. Nat. Prod., 72: 507-515.*
Alley et al., 1988, Feasibility of Drug Screening with Panels of Human Tumor Cell Lines Using a Microculture Tetrazolium Assay, Cancer Research, 48: 589-601.*
Yung et al., 1989, In vitro chemosensitivity testing and its clinical application in human gliomas, Neurosurg. Rev., 12: 197-203.*
Scudiero et al., 1988, Evaluation of a Soluble Tetrazolium/Formazan Assay for Cell Growth and Drug Sensitivity in Culture Using Human and Other Tumor Cell Lines, Cancer Research, 48: 4827-4833.*
Bai, R., et al., "Dolastatin 15, a potent antimitotic depsipeptide derived from *Dolabella auricularia*. Interaction with tubulin and effects on cellular microtubules," 1-Pharmacology Abstract, vol. 117:103735g. p. 41 (1992).
Bai, R., et al., "Structure-Activity Studies with Chiral Isomers and with Segments of teh Antimitotic Marine Peptide Dolastatin 10," Biochemical Pharmacology, vol. 40(8):1859-1864 (1990).

(Continued)

*Primary Examiner* — Amber D Steele
(74) *Attorney, Agent, or Firm* — Lathrop & Gage LLP; Brian C. Trinque

(57) ABSTRACT

The present invention provides antineoplastic peptides of formula I,

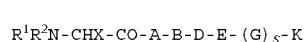

wherein $R^1$, $R^2$, X, A, B, D, E, G, K and s have the meanings stated in the description. The compounds have antineoplastic activity.

18 Claims, No Drawings

OTHER PUBLICATIONS

Kingston, David G.I., "Tubulin-Interative Natural Products as Anti-cancer Agents," J. Nat. Prod., vol. 72:507-515 (2009).

Miyazaki, K., et al., "Synthesis and Antitumor Activity of Novel Dolastatin-10 Analogs," Chem. Pharm. Bull., vol. 43 (10):1706-1718 (1995).

Pettit, G.R., et al., "Antineoplastic Agents. 220. Synthesis of Natural (−)-Dolastatin 15," J. Chem. Soc., vol. 113:6692-6693 (1991).

Pettit, G.R., et al., "Antineoplastic Agents 337. Synthesis of Dolastatin-10 Structural Modifications," Anti-Cancer Drug Design, vol. 10:529-544 (1995).

Pettit, G.R., et al., "Isolation and Structure of the Cytostatic Depsipeptide Dolastatin 13 from the Sea Hare *Dolabella auricularia*," J. Am. Chem. Soc., vol. 111(13):5015-5017 (1989).

Pettit, G.R., et al., "Isolation and Structure of the Cytostatic Linear Depsipeptide Dolastatin 15," J. Org. Chem. vol. 54:6005-6006 (1989).

Pettit, G.R., et al., "Isolation of Dolastatin 10-15 from the Marine Mollusc *Dolabella auricularia*," Tetrahedron, vol. 49 (42):9151-9170 (1993).

Pettit, G.R., et al., "The Dolastatins 20. A convenient synthetic route to Dolastatin 15," Tetrahedron, vol. 50 (42):12097-12108 (1994).

Pettit, G.R., et al., "The Isolation and Structure of a Remarkable Marine Animal Antineoplastic Constituent: Dolastatin 10," J. Am. Chem. Soc., vol. 109:6883-6885 (1987).

Rasila, Kanwaldeep Kaur et al., "Tasidotin HCI Genzyme," Current Opinion in Investigational Drugs, vol. 6(6):631-638 (2005).

Voskoglou-Nomikos, Theodora et al., "Clinical Predictive Value of the in Vitro Cell Line, Human Xenograft, and Mouse Allograft Preclinical Cancer Models," Clinical Cancer Research, vol. 9:4227-4239 (2003).

* cited by examiner

```
                              SEQUENCE LISTING

<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (3)
<223> OTHER INFORMATION: MeVal

<400> SEQUENCE: 1

Val Val Val Pro Pro
  1               5

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (3)
<223> OTHER INFORMATION: MeVal

<400> SEQUENCE: 2

Val Val Val Pro
  1
```

ANTINEOPLASTIC PEPTIDES

RELATED APPLICATIONS

This application is a continuation of U.S. patent application Ser. No. 12/079,980, filed Mar. 31, 2008 which issued as U.S. Pat. No. 7,807,779, which is a divisional of U.S. patent application Ser. No. 11/179,074, filed Jul. 11, 2005 which issued as U.S. Pat. No. 7,368,528 on May 6, 2008, which is a divisional of U.S. patent application Ser. No. 09/757,142, filed Jan. 9, 2001, now abandoned, which is a continuation of U.S. patent application Ser. No. 09/097,184, filed Jun. 12, 1998, now abandoned, which is a continuation-in-part of International Application Serial No. PCT/EP96/05518, filed Dec. 11, 1996, which designated the United States, published in English, which claims priority to U.S. Provisional Patent Application Ser. No. 60/059,062, entitled "Antineoplastic Peptides", which resulted from the conversion of U.S. patent application Ser. No. 08/573,422, filed Dec. 15, 1995, now abandoned.

The entire teachings of the above applications are incorporated herein by reference.

FIELD OF THE INVENTION

The invention described herein provides novel peptides and derivatives thereof which offer potentially improved therapeutic utilities for the treatment of neoplastic diseases as compared to dolastatin-10 and -15 (U.S. Pat. Nos. 4,879,276 and 4,816,444) and the compounds described in WO 93/23424.

SUMMARY OF THE INVENTION

Compounds of this invention include novel peptides of the formula i $$R^1R^2N\text{-}CHX\text{-}CO\text{-}A\text{-}B\text{-}D\text{-}E\text{-}(G)_S\text{-}K \qquad I$$

where

| | |
|---|---|
| $R^1$ | is hydrogen, methyl, or ethyl; |
| $R^2$ | is methyl; or ethyl; or |
| $R^1\text{—}N\text{—}R^2$ | together are a pyrrolidine ring; |
| A | is a valyl, isoleucyl, alto-isoleucyl, 2-tert-butyiglycyl, 2-ethylglycyl, norleucyl or norvalyl residue; |
| B | is a N-methyl-valyl, N-methyl-norvalyl, N-methyl-leucyl, N-methyl-isoleucyl, N-methyl-2-tert-butylglycyl, N-methyl-2-ethylglycyl, or N-methyl-norleucyl residue; |
| D | is a prolyl, homoprolyl, hydroxyprolyl, or thiazolidine-4-carbonyl residue; |
| E | is a prolyl, homoprolyl, hydroxyprolyl, or thiazolidine-4-carbonyl, trans-4-fluoro-L-prolyl, cis-4-fluoro-L-prolyl, trans-4-chloro-L-prolyl or cis-4-chloro-L-prolyl residue; |
| X | is ethyl, propyl, butyl, isopropyl, sec. butyl, tert.-butyl, cyclopropyl, or cyclopentyl; |
| G | is a L-2-tert.butylglvcyl, D-2-tert.butylglycyl, D-valyl, D-isoleucyl, D-leucyl, D-norvalyl, 1-aminopentyl-1-carbonyl, or 2,2-dimethylglycyl residue; |
| S | is 0 or 1; |
| K | is —NH—$C_{1-8}$-alkyl, —NH—$C_{3-8}$-alkenyl, —NH—$C_{3-8}$-alkinyl, —NH—$C_{6-8}$ cycloalkyl, —NH—$C_{1-4}$-alkene—$C_{3-8}$cycloalkyl, $C_{1-4}$-alkyl—N—$C_{1-6}$-alkyl, in which residues one $CH_2$ group may be replaced by O or S, one H by phenyl or cyano, or 1, 2 or 3 H by F, except the N-methoxy-N-methylamino, N-benzylamino, or N-methyl-N-benzylamion residue, or K is |

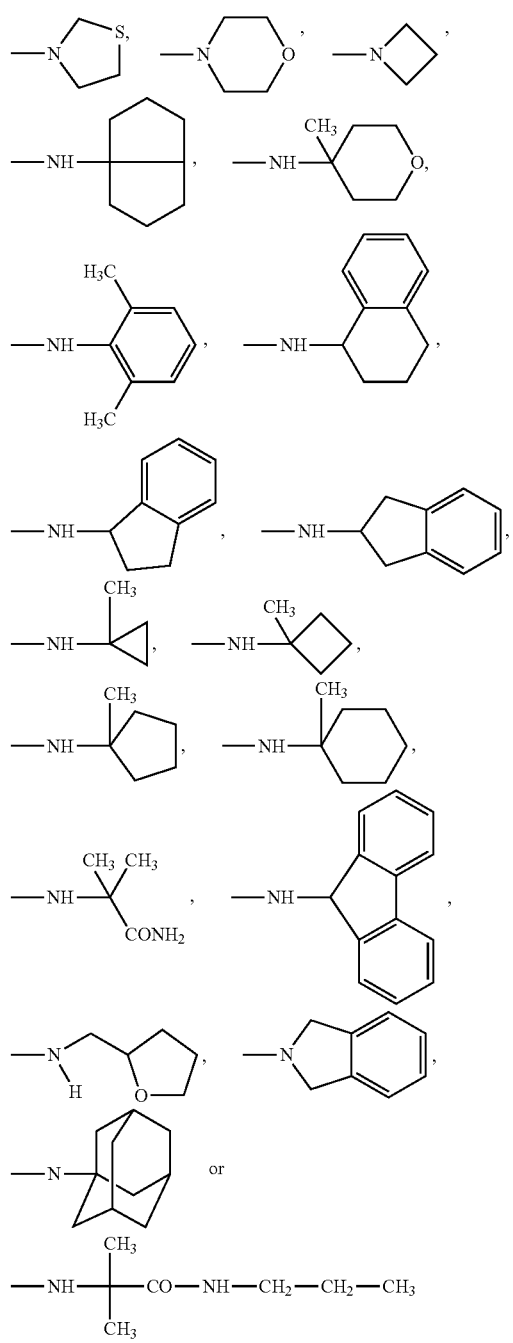

and the salts thereof with physiologically tolerated acids

DETAILED DESCRIPTION OF THE INVENTION

In specific embodiments of the compounds of formula I, K may be —NHCH$_3$, —NHCH$_2$CH$_3$, —NH(CH$_2$)$_2$CH$_3$, —NH(CH$_2$)$_3$CH$_3$, —NH(CH$_2$)$_4$—CH$_3$, —NH(CH$_2$)$_5$CH$_3$, —NH(CH$_2$)$_6$CH$_3$, —NHCH(CH$_2$)$_7$CH$_3$, —NHCH(CH$_3$)$_2$, —NHCH(CH$_3$)CH$_2$CH$_3$, —NHCH(CH$_2$CH$_3$)$_2$, —NHCH(CH$_2$CH$_2$CH$_3$)$_2$, NHC(CH$_3$)$_3$, NHCH(CH$_2$CH$_3$)CH$_2$CH$_2$CH$_3$, —NHCH(CH$_3$)CH(CH$_3$)$_2$, —NHCH(CH$_2$CH$_3$)CH(CH$_3$)$_2$, —NHCH(CH$_3$)C(CH$_3$)$_3$, —NH-cyclohexyl, —NH-cycloheptyl, —NH-cyclooctyl, —N(CH$_3$)OCH$_2$CH$_3$, N(CH$_3$)OCH$_2$CH$_2$CH$_3$, —N(CH$_3$)OCH(CH$_3$)$_2$, —N(CH$_3$)O(CH$_2$)$_3$, —N(CH$_3$)OCH$_2$C$_6$H$_5$, —NH(CH$_2$)$_2$C$_6$H$_5$, —NH(CH$_2$)$_3$C$_6$H$_5$, —NHCH(CH$_3$)C$_6$H$_5$, —NHC(CH$_3$)$_2$C$_6$H$_5$, —NHC(CH$_3$)$_2$CH$_2$CH$_3$, —NHC(CH$_3$)(CH$_2$CH$_3$)$_2$, —NHCH[CH(CH$_3$)$_2$]$_2$), —NHC(CH$_3$)$_2$CN, —NHCH(CH$_3$)CH(OH)C$_6$H$_5$, —NHCH$_2$-cyclohexyl, NHCH$_2$C(CH$_3$)$_3$, —NHCH$_2$CH(CH$_3$)$_2$, —N(CH$_3$)$_2$, —N(CH$_2$CH$_3$)$_2$, —N(CH$_2$CH$_2$CH$_3$)$_2$, —NHCH$_2$CF$_3$, —NHCH(CH$_2$F)$_2$, —NHCH$_2$CH$_2$F, —NHCH$_2$CH$_2$OCH$_3$, —NHCH$_2$CH$_2$SCH$_3$, —NHCH$_2$CHCH$_2$, —NH—C(CH$_3$)$_2$CH=CH$_2$, —NHC(CH$_3$)$_2$C≡CH, —NHC(CH$_2$CH$_3$)$_2$C≡CH, —NHC(CH$_3$)$_2$CH$_2$OH, —NH(CH$_2$CH$_2$O)$_2$CH$_2$CH$_3$, —NHC(CH$_3$)$_2$CH(CH$_3$)$_2$, —NHC(CH$_3$)$_2$CH$_2$CH$_2$CH$_3$, —NHC(CH$_3$)$_2$CH$_2$—C$_6$H$_5$, —N(OCH$_3$)CH(CH$_3$)$_2$—N(OCH$_3$)CH$_2$CH$_3$, —N(OCH$_3$)CH$_2$CH$_2$CH$_3$, —N(OCH$_3$)CH$_2$C$_6$H$_5$, —N(OCH$_3$)C$_6$H$_5$, —N(CH$_3$)OC$_6$H$_5$, —NHCH[CH(CH$_3$)$_2$]$_2$, —N(OCH$_3$)CH$_2$CH$_2$CH$_2$CH$_3$, or the special ring systems mentioned above.

In one embodiment of the compounds of formula I described above, s is 0 and E is homoprolyl or hydroxyprolyl.

Preferred are compounds of the formula I where the substituents R$^1$, R$^2$, A, B, D, E, X, G and s have the following meanings:

R$^1$ hydrogen, methyl, or ethyl, especially methyl;
R$^2$, methyl or ethyl, especially methyl;
A valyl, valyl, isoleucyl, 2-tert-butylglycyl, 2-ethylglycyl, norleucyl or norvalyl, especially valyl, isoleucyl, 2-tert-butylglycyl, 2-ethiyigivcyl,
B N-methyl-valyl, N-methyl-norvalyl, N-methyl-isoleucyl, N-methyl-2-tert-butylglycyl, N-methyl-2-ethylglycyl, or N-methyl-norleucyl, especially N-methyl-valyl, N-methyl-2-ethylglycyl, N-methyl-norleucyl, N-methyl-isoleucyl, or N-methyl-2-tert.butyl-glycyl;
D prolyl, homoprolyl or thiazolidine-4-carbonyl, especially prolyl or thiazolidine-4-carbonyl;
E prolyl, homoprolyl, thiazolidine-4-carbonyl, trans-4-fluoro-L-prolyl, cis-4-fluoro-L-prolyl, trans-4-chloro-L-prolyl or cis-4-chloro-L-prolyl, especially prolyl, trans-4-fluoro-prolyl, cis-4-fluoro-prolyl, trans-4-chloro-prolyl, or cis-4-chloro-prolyl;
X ethyl, propyl, isopropyl, sec.butyl, tert.butyl or cyclo-propyl, especially ethyl, isopropyl, sec.butyl or tert.butyl;
G L-2-tert.butylglycyl, D-2-Tert.butylglycyl, D-valyl, D-isoleucyl, D-leucyl or 2,2-dimethylglycyl residue;
s 0 or 1.

Preferred meanings for K are:
—NH—C$_{1-8}$-alkyl, —NH—C$_{6-8}$-cycloalkyl, —NH—CH$_2$-cyclohexyl, C$_{1-4}$-alkyl-N—C$_{1-6}$-alkyl, in which residues one CH$_2$ group may be replaced by O, one H by phenyl or 1 or 2 H by F, except the N-methoxy-N-methylamino, N-benzylamino, or N-methyl-N-benzylamino residue, or K is

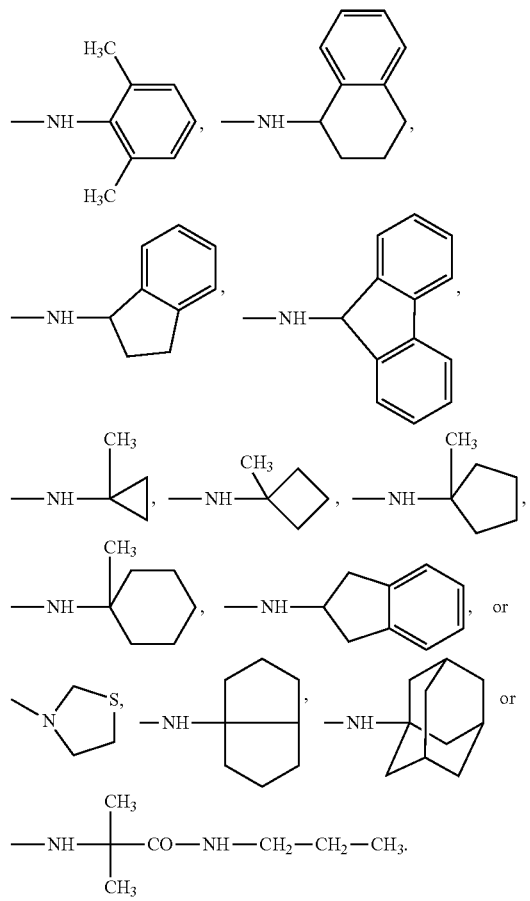

More preferred K is
—NHCH$_3$, —NHCH$_2$CH$_3$, —NH(CH$_2$)$_2$CH$_3$, —NH(CH$_2$)$_3$CH$_3$, —NH(CH$_2$)$_4$—CH$_3$, —NH(CH$_2$)$_5$CH$_3$, —NH(CH$_2$)$_6$CH$_3$, —NH(CH$_2$)$_7$CH$_3$, —NHCH(CH$_3$)$_2$, —NHCH(CH$_3$)CH$_2$CH$_3$, —NHCH(CH$_2$CH$_3$)$_2$, —NHCH(CH$_2$CH$_2$CH$_3$)$_2$, —NHC(CH$_3$)$_3$, —NHCH(CH$_2$CH$_3$)CH$_2$CH$_2$CH$_3$, —NHCH(CH$_3$)CH(CH$_3$)$_2$, —NHCH(CH$_2$CH$_3$)CH(CH$_3$)$_2$, —NHCH(CH$_3$)C(CH$_3$)$_3$, —NH-cyclohexyl, —NH-cycloheptyl, —NH-cyclooctyl, —N(CH$_3$)OCH$_2$CH$_3$, —N(CH$_3$)OCH$_2$CH$_2$CH$_3$, —N(CH$_3$)OCH(CH$_3$)$_2$, —N(OCH$_3$)CH(CH$_3$)$_2$, —N(CH$_3$)OCH$_2$C$_6$H$_5$, —NH(CH$_2$)$_2$C$_6$H$_5$, —NH(CH$_2$)$_3$C$_6$H$_5$, —NHCH(CH$_3$)C$_6$H$_5$, —NHC(CH$_3$)$_2$C$_6$H$_5$, —NHC(CH$_3$)$_2$CH$_2$CH$_3$, —NHC(CH$_3$)(CH$_2$CH$_3$)$_2$, —NHC(CH$_3$)CH(OH)C$_6$H$_5$, —NHCH$_2$-cyclohexyl, —N(CH$_3$)$_2$, —N(CH$_2$CH$_3$)$_2$, —N(CH$_2$CH$_2$CH$_3$)$_2$, —NHCH(CH$_2$F)$_2$, —NHC(CH$_3$)CH=CH$_2$, —NHC(CH$_3$)$_2$CN, —NHC(CH$_3$)$_2$C≡CH, —NHC(CH$_3$)$_2$CONH$_2$, —NHCH[CH(CH$_3$)$_2$]$_2$, —N(OCH$_3$)CH$_2$C$_6$H$_5$, —N(OCH$_3$)CH$_2$CH$_3$, —N(OCH$_3$)CH$_2$CH$_2$CH$_3$, —N(OCH$_3$)CH$_2$CH$_2$CH$_2$CH$_3$,

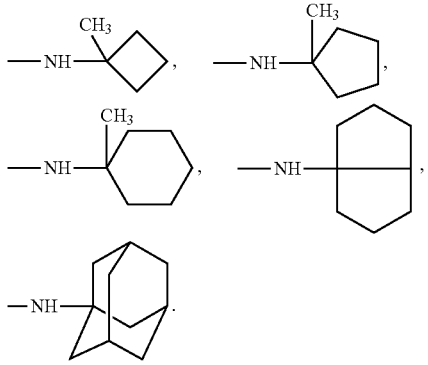

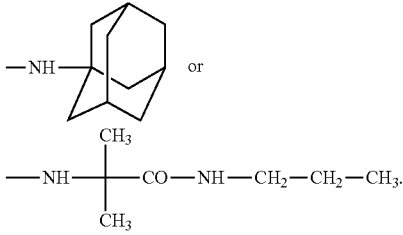

In one embodiment of the preferred compounds of formula I described above, is 0 and E is homoprolyl or hydroxyprolyl.

Especially preferred are compounds of the formula I where $R^1$ and $R^2$ are methyl, A is a valyl, isoleucyl, 2-tert.-butylglycyl residue B is a N-methylvalyl, N-methyl-isoleucyl, methyl-2tert.-butylglyeyl residue, D is a prolyl or thiazolidine-4-carbonyl residue E is a prolyl, cis-4-fluoro-L-prolyl, or cis-4-chloro-L-prolyl residue X is a isopropyl, sec.-butyl, or tert.-butyl residue, s is 0 and K is —NHCH(CH$_3$)$_2$, —NHCH(CH$_3$)CH$_2$CH$_3$, —NHCH(CH$_2$CH$_3$)$_2$, —NHCH(CH$_2$CH$_2$CH$^3$)$_2$, —NHC(CH$_3$)$_3$, —NHCH(CH$_2$CH$_3$)CH$_2$CH$_2$CH$_3$, —NHCH(CH$_3$)CH(CH$_3$)$_2$, —NHCH(CH$_2$CH$_3$)CH(CH$_3$)$_2$, —NHCH(CH$_3$)C(CH$_3$)$_3$, —NH-cycloheptyl, —NH-cyclooctyl, —N(CH$_3$)OCH$_2$CH$_3$, —N(CH$_3$)OCH$_2$CH$_2$CH$_3$, —N(CH$_3$)OCH(CH$_3$)$_2$, —N(OCH$_3$)CH(CH$_3$)$_2$, —N(CH$_3$)OCH$_2$C$_6$H$_5$, —NH(CH$_2$)$_2$C$_6$H$_5$, —NH(CH$_2$)$_3$C$_6$H$_5$, —NHCH(CH$_3$)C$_6$H$_5$, —NHC(CH$_3$)$_2$C$_6$H$_5$, —NHC(CH$_3$)$_2$CH$_2$CH$_3$, NHC(CH$_3$)(CH$_2$CH$_3$)$_2$, —NHCH(CH$_3$)CH(OH)C$_6$H$_5$, —NHCH(CH$_2$F)$_2$, —NHC(CH$_3$)$_2$CH$_2$CH$_2$OH, —NH(CH$_2$CH$_2$O)$_2$CH$_7$CH$_3$, —NHC(CH$_3$)$_2$CH═CH$_2$, —NHC(CH$_3$)$_2$CH(CH$_3$)$_2$, —N(OCH$_3$)CH$_2$CH$_3$, —N(OCH$_3$)CH$_2$CH$_2$CH$_3$, —N(OCH$_3$)CH$_2$CH$_2$CH$_2$CH$_3$, —NHC(CH$_3$)$_2$CN, —NHC(CH$_3$)$_2$C≡CH, —NHCH[CH(CH$_3$)$_2$]$_2$, —NHC(CH$_3$)$_2$CONH$_2$, —NHC(CH$_3$)$_2$CH$_2$C$_6$H$_5$, —N(OCH$_3$)C$_6$H$_5$, —N(OCH$_3$)CH$_2$C$_6$H$_5$,

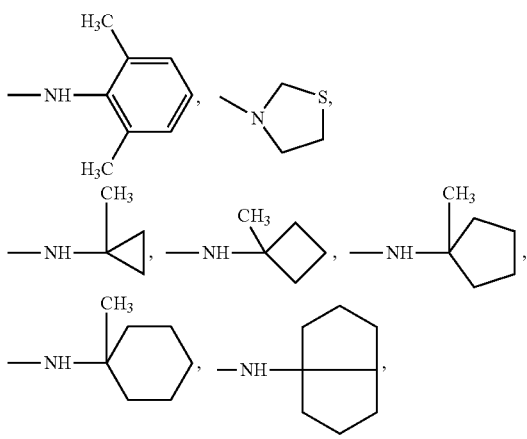

This invention also provides methods for preparing the compounds of formula I, pharmaceutical compositions containing such compounds together with a pharmaceutically acceptable carrier and methods for using same for treating cancer in mammals.

The new compounds may be present as salts with physiologically tolerated acids such as: hydrochloric acid, citric acid, tartaric acid, lactic acid, phosphoric acid, methanesulfonic acid, acetic acid, formic acid, fumaric acid, malic acid, succinic acid, malonic acid, sulfuric acid, L-glutamic acid, L-aspartic acid, pyruvic acid, mucic acid, benzoic acid, glucuronic acid, oxalic acid, ascorbic acid and acetylglycine.

The novel compounds can be prepared by known methods of peptide chemistry. Thus, the peptides can be assembled sequentially from amino acids or by linking suitable small peptide fragments. In the sequential assemblage, starting at the C terminus the peptide chain is extended stepwise by one amino acid each time. In fragment coupling it is possible to link together fragments of different lengths, and the fragments in turn can be obtained by sequential assemblage from amino acids or themselves by fragment-coupling.

Both in the sequential assemblage and in the fragment coupling it is necessary to link the units by forming an amide linkage. Enzymatic and chemical methods are suitable for this.

Chemical methods for forming the amide linkage are described in detail by Mueller, Methoden der organischen Chemie Vol. XV/2, pp 1 to 264, Thieme Verlag, Stuttgart, 1974; Stewart, Young, Solid Phase Peptide Synthesis, pp 31 to 34, 71 to 82, Pierce Chemical Company, Rockford, 1984; Bodanszky, Klausner, Ondetti, Peptide Synthesis, pp 85 to 128, John Wiley & Sons, New York, 1976; The Practice of Peptide Synthesis, M. Bodanszky, A. Bodanszky, Springer-Verlag, 1994, and other standard works on peptide chemistry. Particular preference is given to the azide method, the symmetric and mixed anhydride method, in situ generated or performed active esters, the use of urethane protected N-carboxy anhydrides of amino acids and the formation of the amide linkage using coupling reagents, especially dicyclohexylcarbodiimide (DCC), diisopropylcarbodiimide (DIC), 1-ethoxycarbonyl-2-ethoxy-1,2-dihydroquinoline (EEDQ), pivaloylchloride, 1-ethyl-3-(3-dimethylaminopropyl)carbodiimide hydrochloride (EDCI), n-propanephosphonic anhydride (PPA), N,N-bis(2-oxo-3-oxazolodinyl)-amidophosphoryl chloride (BOP-Cl), bromo-tris-pyrrolidino-phosphonium hexafluororophosphate (PyBrop), diphenylphosphoryl azide (DPPA), Castro's reagent (BOP, PyBop), O-benzotriazolyl-N,N,N',N'-tetramethyluronium salts (HBTU), O-azabenzotriazolyl-N,N,N',N'-tetramethyluronium salts (HATU), diethylphosphoryl cyanide (DEPCN), 2,5-diphenyl-2,3-dihydro-3-oxo-4-hydroxythiophene dioxide (Steglich's reagent; HOTDO) and 1,1'-carbonyldiimidazole (CDI). The coupling reagents can be employed alone or in combination with additives such as N,N-dimethyl-4-aminopyridine (DMAP), N-hydroxy-benzotriazole (HOBt, N-hydroxybenzotriazine (HOOBt), Azabenzotriazole, N-hydroxysuccinimide (HOSu) or 2-hydroxypyridine.

Whereas it is normally possible to dispense with protective groups in enzymatic peptide synthesis, reversible protection of reactive groups not involved in formation of the amide linkage is necessary for both reactants in chemical synthesis. Three conventional protective group techniques are preferred for the chemical peptide synthesis: the benzyloxycarbonyl (Z), the t-butoxycarbonyl (Boc) and the 9-fluorenylmethoxycarbonyl (Fmoc) techniques.

Identified in each case is the protective group on the alpha-amino group of the chain-extending unit. A detailed review of amino-acid Protective groups is given by Mueller, Methoden der organischem Chemie vol. XV/1, pp 20 to 906, Thieme Verlag, Stuttgart, 1974. The units employed for assembling the peptide chain can be reacted in solution, in suspension or by a method similar to that described by Merrifield in J. Amer. Chem. Soc. 85 (1963) 2149.

Suitable for peptide synthesis in solution are all solvents which are inert under the reaction conditions, especially water, N,N-dimethylformamide (DMF), dimethylsulfoxide (DMSO), acetonitrile, dichloromethane (DCM), ethyl acetate, 1,4-dioxane, tetrahydrofuran (THF), N-methyl-2-pyrrolidone (NMP) and mixtures of the said solvents.

Peptide synthesis on the polymeric support can be carried out in all inert organic solvents in which the amino-acid derivatives used are soluble. However, preferred solvents additionally have resin-swelling properties, such as DMF, DCM, NMP, acetonitrile and DMSO, and immixtures of these solvents. After synthesis is complete, the peptide is cleaved off the polymeric support. The conditions under which cleavage off the various resin types is possible are disclosed in the literature. The cleavage reactions most commonly used are acid- and palladium-catalyzed, especially cleavage in liquid anhydrous hydrogen fluoride, in anhydrous trifluoromethanesulfonic acid, in dilute or concentrated trifluoroacetic acid, palladium-catalyzed cleavage in THF or THF-DCM mixturers in the presence of a weak base such as morpholine or cleavage in acetic acid/dichloromethane/trifluoroethanol mixtures. Depending on the chosen protective groups, these may be retained or likewise cleaved off under the cleavage conditions.

Partial deprotection of the peptide may also be worthwhile when certain derivatization reactions are to be carried out.

Peptides dialkylated at the N-terminus can be prepared either by coupling on the appropriate N,N-di-alkylamino acids in solution or on the polymeric support, by reductive alkylation of the resin-bound peptide in DMF/1% acetic acid with NaCNBH$_3$ and the appropriate aldehydes, by hydrogenation of the peptide in solution in the presence of aldehyde or ketone and Pd/C.

The various non-naturally occurring amino acids as well as the various non-amino acid moieties disclosed herein may be obtained from commercial sources or synthesized from commercially available materials using methods known in the art. For example, amino acids building blocks with $R^1$ and $R^2$ moieties can be prepared according to E. Wuensch, Houben Weyl, Meth. d. Org. Chemie, Bd. XV, 1, p. 306 following, Thieme Verlag Stuttgart 1974 and Literature cited therein.

The compounds of this invention may be used to inhibit or otherwise treat solid tumors (e.g. tumors of the lung, breast, colon, prostate, bladder, rectum, or endometrial tumors) or hematological malignancies (e.g. leukemias, lymphomas) by administration of the compound to the mammal.

It is a special advantage of the new compounds that they are very resistant to enzymatic degradation and can also be administered orally.

Administration may be by any of the means which are conventional for pharmaceutical, preferably oncological, agents, including oral and parenteral means such as subcutaneously, intravenously, intramuscularly and intraperitoneally.

The compounds may be administered alone or in the form of pharmaceutical compositions containing a compound of formula I together with a pharmaceutically accepted carrier appropriate for the desired route of administration. Such pharmaceutical compositions may be combination products, i.e., may also contain other therapeutically active ingredients.

The dosage to be administered to the mammal will contain an effective tumor-inhibiting amount of active ingredient which will depend upon conventional factors including the biological activity of the particular compound employed; the means of administration; the age, health and body weight of the recipient; the nature and extent of the symptoms; the frequency of treatment; the administration of other therapies; and the effect desired. A typical daily dose will be about 0.05 to 50 milligrams per kilogram of body weight on oral administration and about 0.01 to 20 milligrams per kilogram of body weight on parenteral administration.

The novel compounds can be administered in conventional solid or liquid pharmaceutical administration forms, e.g. uncoated or (film-)coated tablets, capsules, powders, granules, suppositories or solutions. These are produced in a conventional manner. The active substances can for this purpose be processed with conventional pharmaceutical aids such as tablet binders, fillers preservatives, tablet disintegrants, flow regulators, plasticizers, wetting agents, dispersants, emulsifiers, solvents, sustained release compositions, antioxidants and/or propellant gases (cf. H. Sucker et al.: Pharmazeutische Technologie, Thieme-Verlag, Stuttgart, 1978). The administration forms obtained in this way normally contain 1-90% by weight of the active substance. The following examples are intended to illustrate the invention. The proteinogenous amino acids are abbreviated in the examples using the known three-letter code. Other abbreviations used: Me$_2$Val=N,N-dimethylvaline, MeVal=N-methylvaline.

EXAMPLES

A. General Procedures

I. The Peptides of the Present Invention are either Synthesized by Classical Solution Synthesis Using Standard Z- and Boc-Methodology as Described above or by Standard Methods of Solid-Phase Synthesis Using Boc and Fmoc Protective Group Techniques.

In the case of solid phase synthesis, the N,N-dialkylpenta- or hexapeptide acids are liberated from the solid support and further coupled with the corresponding C-terminal amines in solution. BOP-Cl and PyBrop were used as reagents for coupling of the amino acid following the N-methylamino acids. The reaction times were correspondingly increased. For reductive alkylation of the N-terminus, the peptide-resin was deprotected at the N terminus and then reacted with a 3-fold molar excess of aldehyde or ketone in DMF/1% acetic acid with addition of 3 equivalents of NaCNBH$_3$. After the reaction was complete (negative Kaisertest) the resin was washed several times with water, isopropanol, DMF and dichloromethane.

In solution synthesis, the use of either Boc-protected amino acid NCAs (N-tert.-butyloxycarbonyl-amino acid-N-carboxy-anhydrides), Z-protected amino acid NCAs (N-benzyloxycarbonyl-amino acid-N-carboxy-anhydrides), or the use of pivaloylchloride as condensing agent respectively is most advantageous for coupling of the amino acid following the N-methylamino acids. Reductive alkylation of the N terminus can e.g. be achieved by reaction of the N-terminally deprotected peptides or amino acids with the corresponding aldehydes or ketones using NaCNBH₃ or hydrogen, Pd/C.

II. Purification and Characterization of the Peptides

Purification was carried out by gel chromatography (SEPHADEX G-10, G-15/10% HOAc, SEPHADEX LH20/MeOH), medium pressure chromatography (stationary phase: HD-SIL C-18, 20-45 mikron, 100 Angstrom; mobile phase: gradient with A=0.1% TFA/MeOH, B=0.1% TFA/water), or preparative HPLC (stationary phase: Waters Delta-Pak C-18, 15 mikron, 100 Angstrom; mobile phase: gradient with A=0.1% TFA/MeOH, 3=0.1% TFA/water).

The purity of the resulting products was determined by analytical HPLC (stationary phase: 100 2.1 mm VYDAC C-18, 5 1, 300 A; mobile phase: acetonitrile-water gradient, buffered with 0.1% TFA, 40.degree. C.).

Characterization was by amino-acid analysis and fast atom bombardment mass spectroscopy.

B. Specific Procedures

```
    Example 1
                                          (SEQ ID NO: 1)
    Me.₂Val-Val-MeVal-Pro-Pro-NHCH(CH₃)₂ a)  Z-MeVal-Pro-OME
```

66.25 g (250 mmol) Z-MeVal-OH were dissolved in 250 ml dry dichloromethane. After addition of 36.41 ml (262.5 mmol) triethylamine, the reaction mixture was cooled to −25° C. and 32.27 ml (262.5 mmol) pivaloyl chloride were added. After stirring for 2.5 h, 41.89 g (250 mmol) H-Pro-OMe×Ch1 in 250 ml dichloromethane, neutralized with 36.41 ml (262.5 mmol) triethylamine at 0.degree. C., were added to the reaction mixture. Stirring continued for 2 h at −25.degree. C. and overnight at room temperature. The reaction mixture was diluted with dichloromethane and thoroughly washed with saturated aqueous NaHCO₃ solution (3×.), water (1×), 5% citric acid (3×) and saturated NaCl solution. The organic phase was dried over sodium sulfate and evaporated to dryness. The residue (91.24 g) was stirred with petroleum ether overnight and filtered. 62.3 g of product were obtained.

```
    b)  H-MeVal-Pro-OMe
```

48.9 g (130 mmol) Z-MeVal-Pro-OMe were dissolved in 490 ml methanol. After addition of 10.9 ml (130 mmol) concentrated hydrochloric acid and 2.32 g 10% Palladium/charcoal, the reaction mixture was hydrogenated. Filtration and evaporation to dryness yielded 36.32 g of the product.

```
    c)  Z-Val-MeVal-Pro-OMe
```

18.1 g (65 mmol) H-MeVal-Pro-OMe, 21.6 g (78 mmol) Z-Val-N-carboxyanhydride and 22.8 ml (130 mmol) diisopropylethylamine were stirred in 110 ml DMF at 40° C. for 2 d. After evaporation of DMF, dichloromethane was added and the organic phase washed with saturated aqueous NaHCO₃ solution (3×), water (1×), 4% citric acid (3×) and saturated NaCl solution. The organic phase was dried over sodium sulfate and evaporated to dryness. The product (29.3 g) was obtained as a viscous oil.

```
    d)  H-Val-MeVal-Pro-OMe
```

29.3 g (61.6 mmol) of Z-Val-MeVal-Pro-OMe were dissolved in 230 ml methanol. After addition of 1.15 g 10% Palladium/charcoal, the reaction mixture was hydrogenated. Filtration and evaporation to dryness yielded 21.96 g of the product.

```
    e)  Z-Val-Val-MeVal-Pro-Ome        (SEQ ID NO: 2)
```

15.29 g (61 mmol) Z-Val-OH and 21.96 g (61 mmol) H-Val-MeVal-Pro-OMe were dissolved in 610 ml dichloromethane and cooled to 0.degree. C. After addition of 8.16 ml (73.2 mmol) N-Methylmorpholine, 2.77 g (20.3 mmol) HOBt and 11.73 g (61 mmol) EDCI, the reaction mixture was stirred overnight at room temperature, diluted with dichloromethane and thoroughly washed with saturated aqueous NaHCO₃ solution (3×), water (1×), 5% citric acid (3×) and saturated NaCl solution. The organic phase was dried over sodium sulfate and evaporated to dryness to yield 31.96 g of the product.

```
    f)  Z-Val-Val-MeVal-Pro-OH         (SEQ ID NO: 2)
```

31.96 g (57 mmol) Z-Val-Val-MeVal-Pro-OMe (SEQ ID NO: 2) were dissolved in 250 ml methanol. 102.6 ml of a 1 N LiOH solution was added and the mixture stirred overnight at room temperature. After addition of 500 ml water, the aqueous phase was washed three times with ethyl acetate, adjusted to pH 2 at 0° C. and extracted three times with ethyl acetate. The organic phase was dried over sodium sulfate and evaporated to dryness yielding 30.62 g of the desired product as a white solid.

```
                                          (SEQ ID NO: 1)
    g)      Z-Val-Val-MeVal-Pro-Pro-NHCH(CH₃)₂
```

2 g (3.35 mmol) Z-Val-Val-MeVal-Pro-OH (SEQ ID NO: 2) and 0.664 g (3.35 mmol) H-Pro-NHCH(CH₃)₂ were dissolved in 34 ml of dry dichloromethane. After cooling to 0° C., 1.35 ml (12.1 mmol) N-methylmorpholine, 0.114 g (0.84 mmol) HOBt and 0.645 g (3.35 mmol) EDCI were added and the reaction mixture stirred overnight at room temperature. 80 ml dichloromethane were added and the organic phase thoroughly washed with saturated aqueous NaHCO₃ solution (3×), water (1×), 5% citric acid (3×) and saturated NaCl solution (1×). The organic phase was dried over sodium sulfate and evaporated to dryness to yield 1.96 g of the product which was used in the next reaction without further purification.

```
                                          (SEQ ID NO: 1)
    h)     Me₂ Val-Val-MeVal-Pro-Pro-NHCH(CH₃)₂
```

1.96 g Z-Val-Val-MeVal-Pro-Pro-NHCH(CH₃)₂ (SEQ ID NO: 2) were dissolved in 11 ml methanol. 0.054 g 10% Pd/C were added under nitrogen atmosphere and the reaction mixture hydrogenated at room temperature for 4 h. After addition of 0.86 ml (11.24 mmol) of a 37% aqueous formaldehyde solution and 0.281 g 10% Pd/C, hydrogenation was continued for 5 h. Filtration and evaporation of the solvent gave rise to 2.77 g of crude product. Further purification was achieved by dissolving the peptide in water, adjusting the pH to 2 and extracting the aqueous phase three times with ethyl acetate. The aqueous phase was then adjusted to pH 8-9 and extracted four times with dichloromethane. The organic phase was dried over sodium sulfate to yield 1.37 g of purified product as a white foam. The compound was further purified using medium pressure liquid chromatography (10-50% A in 10 min.; 50-90% A in 320 min.). Fractions containing the product were combined, lyophilized, redissolved in water and the pH adjusted to 9 with 1 N LiOH. After extraction with dichloromethane, the organic phase was dried over sodium sulfate and evaporated to dryness. Lyophilization led to 500 mg of pure product, which was characterized by fast atom bombardment mass spectrometry ([M+H]$^+$=593).

Example 2
(SEQ ID NO: 1)
Me$_2$ Val-Val-MeVal-Pro-Pro-NHC(CH$_3$)$_3$ (SEQ ID NO: 1)
i) Z-Val-Val-MeVal-Pro-Pro-NHC(CH$_3$)$_3$ 2 g (3.35 mmol) Z-Val-Val-MeVal-Pro-OH (SEQ ID NO: 2) and 0.692 g (3.35 mmol) H-Pro-NHC(CH$_3$)$_3$ were dissolved in 34 ml of dry dichloromethane. After cooling to 0° C., 1.35 ml (12.1 mmol) N-methylmorpholine, 0.114 g (0.84 mmol) HOBt and 0.645 g (3.35 mmol) EDCI were added and the reaction mixture stirred overnight at room temperature. 80 ml dichloromethane were added and the organic phase thoroughly washed with saturated aqueous NaHCO$_3$ solution (3×), water (1×), 5% citric acid (3×) and saturated NaCl solution (1×). The organic phase was dried over sodium sulfate and evaporated to dryness to yield 1.8 g of the product which was used in the next reaction without further purification.

(SEQ ID NO: 1)
k) Me$_2$ Val-Val-MeVal-Pro-Pro-NHC(CH$_3$)$_3$ 1.8 g Z-Val-Val-MeVal-Pro-Pro-NHC(CH$_3$)$_3$ (SEQ ID NO: 1) were dissolved in 10 ml methanol. 0.049 g 10% Pd/C were added under nitrogen atmosphere and the reaction mixture hydrogenated at room temperature for 4 h. After addition of 0.86 ml (11.24 mmol) of a 37% aqueous formaldehyde solution and 0.252 g 10% Pd/C, hydrogenation was continued for 5 h. Filtration and evaporation of the solvent gave rise to 1.82 g of crude product. The compound was further purified using medium pressure liquid chromatography 10-50% A in 10 min.; 50-90% A in 320 min.). Fractions containing the product were combined, lyophilized, redissolved in water and the pH adjusted to 9 with 1 N LiOH. After extraction with dichloromethane, the organic phase was dried over sodium sulfate and evaporated to dryness. Lyophilization led to 547 mg of pure product, which was characterized by fast atom bombardment mass spectrometry ([M+H]$^+$=607).

The following compounds were prepared or can be prepared according to examples 1 and 2:

| 3. | Xaa | Val | Xab | Pro | Xac | |
| 4. | Xaa | Val | Xab | Pro | Xad | |
| 5. | Xaa | Val | Xab | Pro | Xae | |
| 6. | Xaa | Val | Xab | Pro | Xaf | |
| 7. | Xaa | Val | Xab | Pro | Xag | |
| 8. | Xaa | Val | Xab | Pro | Xah | |
| 9. | Xaa | Val | Xab | Pro | Xai | |
| 10. | Xaa | Val | Xab | Pro | Xak | |
| 11. | Xaa | Val | Xab | Pro | Xal | |
| 12. | Xaa | Val | Xab | Pro | Xam | |
| 13. | Xaa | Val | Xab | Pro | Xan | |
| 14. | Xaa | Val | Xab | Pro | Xao | |
| 15. | Xaa | Val | Xab | Pro | Xap | |
| 16. | Xaa | Val | Xab | Pro | Xaq | |
| 17. | Xaa | Val | Xab | Pro | Xar | |
| 18. | Xaa | Val | Xab | Pro | Xas | |
| 19. | Xaa | Val | Xab | Pro | Xat | |
| 20. | Xaa | Val | Xab | Pro | Xau | |
| 21. | Xaa | Val | Xab | Pro | Xav | |
| 22. | Xaa | Val | Xab | Pro | Xaw | |
| 23. | Xaa | Val | Xab | Pro | Xax | |
| 24. | Xdd | Val | Xab | Pro | Xay | |
| 25. | Xaa | Val | Xab | Pro | Xaz | |
| 26. | Xaa | Val | Xab | Pro | Xba | |
| 27. | Xaa | Val | Xab | Pro | Xbb | |
| 28. | Xaa | Val | Xab | Pro | Xay | |
| 29. | Xaa | Val | Xab | Pro | Xbd | |
| 30. | Xaa | Val | Xab | Pro | Xbe | |
| 31. | Xaa | Val | Xab | Pro | Xbf | |
| 32. | Xaa | Val | Xab | Pro | Xbg | |
| 33. | Xaa | Val | Xab | Pro | Xbh | |
| 34. | Xaa | Val | Xab | Pro | Xbi | |
| 35. | Xaa | Val | Xab | Pro | Xbk | |
| 36. | Xaa | Val | Xab | Pro | Xbl | |
| 37. | Xaa | Val | Xab | Pro | Xbm | |
| 38. | Xaa | Val | Xab | Pro | Xbn | |
| 39. | Xaa | Val | Xab | Pro | Xb0 | |
| 40. | Xaa | Val | Xab | Pro | Xbp | |
| 41. | Xaa | Val | Xab | Pro | Xbq | |
| 42. | Xaa | Val | Xab | Pro | Xbr | |
| 43. | Xaa | Val | Xab | Pro | Xbx | |
| 44. | Xaa | Val | Xab | Pro | Xbt | |
| 45. | Xaa | Val | Xab | Pro | Xbu | |
| 46. | Xaa | Val | Xab | Pro | Xbv | |
| 47. | Xaa | Val | Xab | Pro | Xbw | |
| 48. | Xaa | Val | Xab | Pro | Xbx | |
| 49. | Xaa | Val | Xab | Pro | Xby | |
| 50. | Xaa | Val | Xab | Pro | Xbz | |
| 51. | Xaa | Val | Xab | Pro | Xca | |
| 52. | Xaa | Val | Xab | Pro | Xcb | |
| 53. | Xaa | Val | Xab | Pro | Xcc | |
| 54. | Xaa | Val | Xab | Pro | Xcd | |
| 55. | Xaa | Val | Xab | Pro | Xce | |
| 56. | Xaa | Val | Xab | Pro | Xcf | |
| 57. | Xaa | Xdf | Xab | Pro | Xay | |
| 58. | Xaa | Val | Xab | Pro | Xch | |
| 59. | Xaa | Val | Xab | Pro | Xci | |
| 60. | Xaa | Val | Xab | Pro | Xck | |
| 61. | Xaa | Val | Xab | Pro | Xcl | |
| 62. | Xaa | Val | Xab | Pro | Xcm | |
| 63. | Xaa | Val | Xab | Pro | Xcn | |
| 64. | Xaa | Val | Xab | Pro | Xco | |
| 65. | Xaa | Val | Xab | Pro | Xcp | |
| 66. | Xaa | Val | Xab | Pro | Xcq | |
| 67. | Xaa | Val | Xab | Pro | Xcr | |
| 68. | Xaa | Val | Xab | Pro | Xcs | |
| 69. | Xaa | Val | Xab | Pro | Xct | |
| 70. | Xaa | Val | Xab | Pro | Xcu | |
| 71. | Xcx | Val | Xab | Pro | Xcv | |
| 72. | Xcx | Val | Xab | Pro | Xcv | |
| 73. | Xaa | Val | Xab | Pro | Pro | Xcy |
| 74. | Xaa | Val | Xab | Pro | Pro | Xcz |
| 75. | Xaa | Val | Xda | Pro | Xcv | |
| 76. | Xaa | Xdb | Xab | Pro | Xcv | |
| 77. | Xdc | Val | Xab | Pro | Xcv | |
| 78. | Xaa | Ile | Xab | Pro | Xcv | |
| 79. | Xdd | Val | Xab | Pro | Xcv | |
| 80. | Xde | Val | Xab | Pro | Xcv | |
| 81. | Xaa | Xdf | Xab | Pro | Xcv | |
| 82. | Xaa | Val | Xab | Pro | Xcg | |
| 83. | Xaa | Val | Xab | Pro | Pro | Xdg |
| 84. | Xaa | Val | Xab | Pro | Pro | Xdh |
| 85. | Xaa | Val | Xab | Pro | Pro | Xdi |
| 86. | Xaa | Val | Xab | Pro | Pro | Xdk |
| 87. | Xaa | Val | Xdl | Pro | Xcv | |
| 88. | Xde | Val | Xab | Pro | Xay | |
| 89. | Xaa | Val | Xdl | Pro | Xay | |
| 90. | Xaa | Val | Xab | Pro | Xdm | |
| 91. | Xaa | Val | Xab | Pro | Xdn | |
| 92. | Xaa | Val | Xab | Pro | Xdo | |
| 93. | Xaa | Val | Xab | Pro | Xdp | |
| 94. | Xaa | Val | Xab | Pro | Xdq | |
| 95. | Xaa | Val | Xab | Pro | Pro | Xdr |
| 96. | Xaa | Val | Xab | Pro | Xds | |
| 97. | Xaa | Val | Xbc | Pro | Xcv | |
| 98. | Xaa | Ile | Xab | Pro | Xay | |
| 99. | Xcw | Val | Xab | Pro | Xay | |

-continued

| | | | | | |
|---|---|---|---|---|---|
| 100. | Xaa | Val | Xbc | Pro | Xal |
| 101. | Xaa | Val | Xdl | Pro | Xal |
| 102. | Xaa | Xdf | Xab | Pro | Xal |
| 103. | Xaa | Ile | Xab | Pro | Xal |
| 104. | Xdd | Val | Xab | Pro | Xal |
| 105. | Xde | Val | Xab | Pro | Xal |
| 106. | XcX | Val | Xab | Pro | Xcy |
| 107. | Xcw | Val | Xab | Pro | Xal |
| 108. | Xcx | Val | Xab | Pro | Xal |
| 109. | Xcw | Val | Xab | Pro | Xav |
| 110. | Xcx | Val | Xab | Pro | Xav |
| 111. | Xcw | Val | Xab | Pro | Xaw |
| 112. | Xcx | Val | Xab | Pro | Xaw |
| 113. | Xab | Val | Xab | Pro | Xay |
| 114. | Xab | Val | Xab | Pro | Xcv |
| 115. | Xab | Val | Xab | Pro | Xal |
| 116. | Xab | Val | Kab | Pro | Xam |
| 117. | Xab | Val | Xab | Pro | Xam |
| 118. | Xab | Val | Xab | Pro | Xao |
| 119. | Xab | Val | Xab | Pro | Xay |
| 120. | Xab | Val | Xab | Pro | Xaw |
| 121. | Xab | Val | Xab | Pro | Xau |
| 122. | Xab | Val | Xab | Pro | Xau |
| 123. | Xab | Val | Xab | Pro | Xbf |
| 124. | Xab | Val | Xab | Pro | Xbm |
| 125. | Xab | Val | Xab | Pro | Xbm |
| 126. | Xab | Val | Xab | Pro | Xbo |
| 127. | Xab | Val | Xab | Pro | Xch |
| 128. | Xaa | Val | Xab | Pro | Xdt |
| 129. | Xaa | Val | Xab | Pro | Xdu |
| 130. | Xaa | Val | Xab | Pro | Xdv |
| 131. | Xaa | Val | Xab | Pro | Xdw |
| 132. | Xaa | Val | Xab | Pro | Xdx |
| 133. | Xaa | Val | Xab | Pro | Xdy |
| 134. | Xaa | Val | Xab | Pro | Xdz |
| 135. | Xaa | Val | Xab | Pro | Xea |
| 136. | Xaa | Val | Xab | Pro | Xeb |
| 137. | Xaa | Val | Xab | Pro | Xec |
| 138. | Xaa | Val | Xab | Pro | Xed |
| 139. | Xaa | Val | Xab | Pro | Xef |
| 140. | Xaa | Val | Xab | Pro | Xeg |
| 141. | Xaa | Val | Xab | Pro | Xeh |
| 142. | Xaa | Val | Xab | Pro | Xei |
| 143. | Xaa | Val | Xab | Pro | Xek |
| 144. | Xaa | Val | Xab | Pro | Xel |
| 145. | Xaa | Val | Xab | Pro | Xem |
| 146. | Xaa | Val | Xab | Pro | Xen |
| 147. | Xaa | Val | Xab | Pro | Xeo |
| 148. | Xaa | Val | Xab | Pro | Xep |
| 149. | Xaa | Val | Xab | Pro | Xeq |
| 150. | Xaa | Val | Xab | Pro | Xer |
| 151. | Xaa | Val | Xab | Pro | Xcg |

Examples for the MS-characterization of the synthesized novel compounds are given in the following table.

TABLE I

Sequence Identification of Compounds Prepared According to Examples 1 and 2

| EXAMPLE [No.] | Fast atom bombardment MS analysis. [Mol.-Weight (measured)] |
|---|---|
| 3. | 565 |
| 4. | 579 |
| 5. | 593 |
| 6. | 607 |
| 7. | 621 |
| 8. | 635 |
| 11. | 607 |
| 12. | 607 |
| 13. | 621 |
| 14. | 649 |
| 15. | 635 |
| 16. | 635 |
| 17. | 635 |
| 18. | 635 |
| 19. | 621 |
| 20. | 621 |
| 21. | 635 |
| 22. | 635 |
| 25. | 633 |
| 26. | 647 |
| 27. | 661 |
| 31. | 623 |
| 32. | 671 |
| 33. | 667 |
| 34. | 631 |
| 35. | 655 |
| 36. | 655 |
| 37. | 669 |
| 38. | 621 |
| 39. | 635 |
| 41. | 649 |
| 42. | 621 |
| 43. | 633 |
| 44. | 667 |
| 45. | 607 |
| 46. | 647 |
| 47. | 668 |
| 48. | 655 |
| 49. | 669 |
| 50. | 685 |
| 51. | 629 |
| 52. | 625 |
| 53. | 721 |
| 55. | 579 |
| 58. | 623 |
| 61. | 597 |
| 62. | 621 |
| 63. | 609 |
| 64. | 625 |
| 65. | 635 |
| 66. | 591 |
| 67. | 715 |
| 68. | 685 |
| 69. | 685 |
| 70. | 591 |
| 71. | 607 |
| 72. | 621 |
| 74. | 706 |
| 75. | 579 |
| 76. | 579 |
| 77. | 579 |
| 78. | 607 |
| 79. | 607 |
| 80. | 607 |
| 81. | 607 |
| 82. | 637 |
| 83. | 692 |
| 84. | 706 |
| 85. | 706 |
| 86. | 706 |
| 87. | 607 |
| 90. | 635 |
| 92. | 659 |
| 93. | 617 |
| 94. | 636 |
| 95. | 678 |
| 128. | 671 |
| 131. | 625 |
| 139. | 625 |
| 151. | 637 |

Compound Number(s)
1-56, 58-72, 75, 77, 79, 80, 82, 87-94, 96, 97, 99-101, 104-151
73, 74, 83-86, 95,
57, 76, 81, 102
78, 98, 103

The symbols Xaa in the summary have the following meanings:
N,N-Dimethylvaline — Xaa
N-Methylvaline — Xab
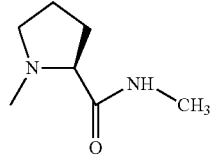 Xac
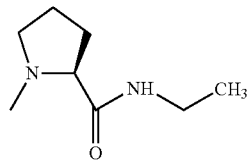 Xad
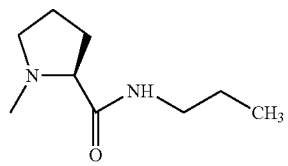 Xae
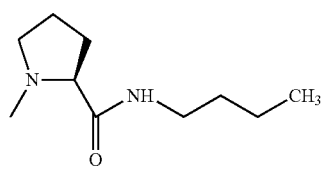 Xaf
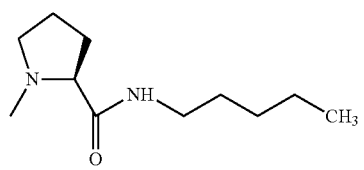 Xag
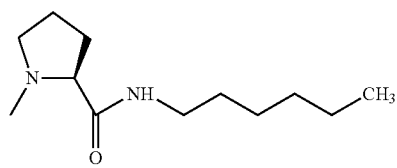 Xah
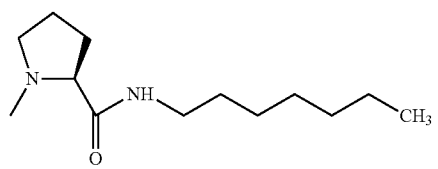 Xai
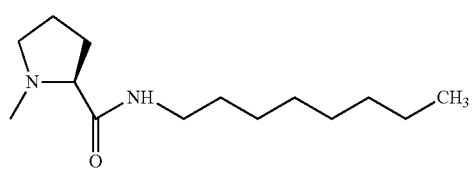 Xak
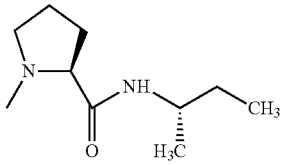 Xal
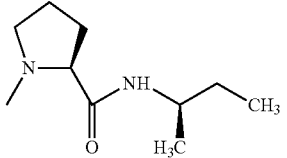 Xam
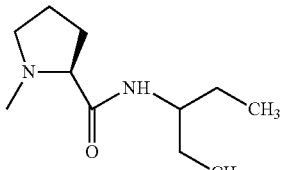 Xan
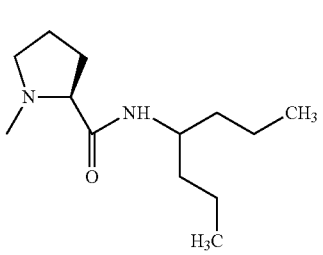 Xao
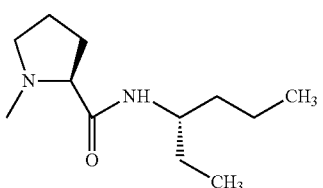 Xap
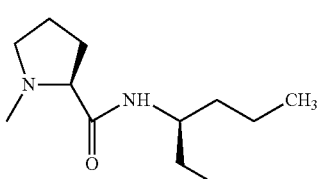 Xaq
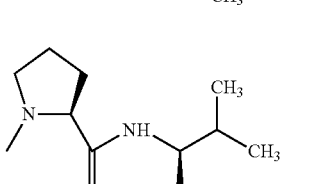 Xar
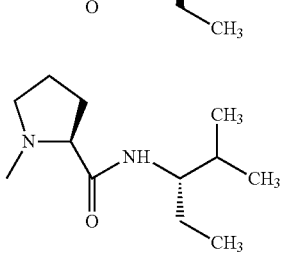 Xas Xat 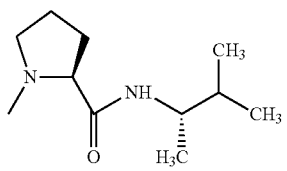
Xau 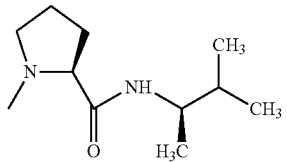
Xav 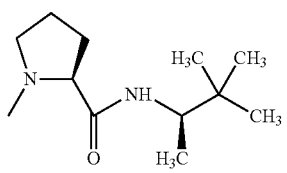
Xaw 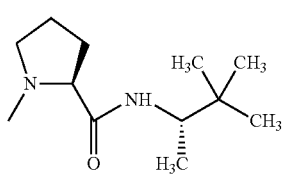
Xax 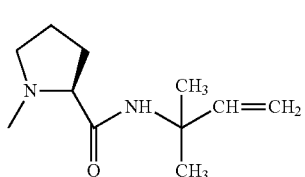
Xay 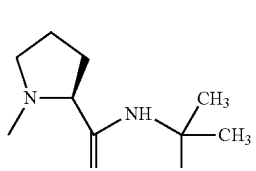
Xaz 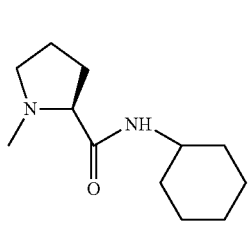
Xba 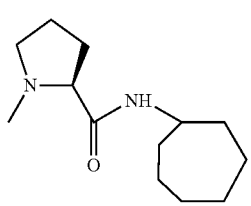
Xbb 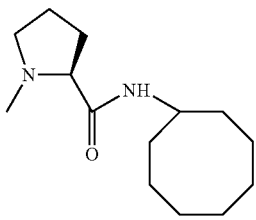
N-Methyl-isoleucine
Xbc
Xbd 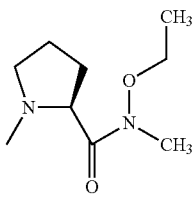
Xbe 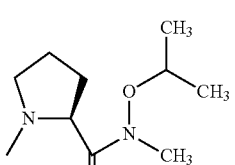
Xbf 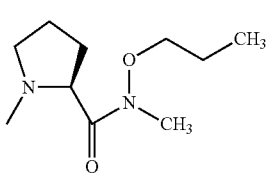
Xbg 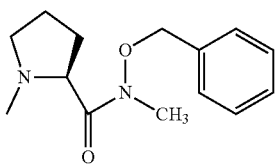
Xbh 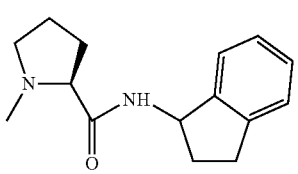
Xbi 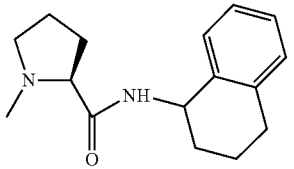
Xbk 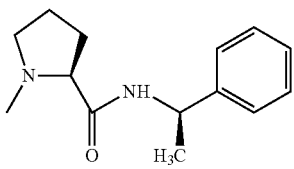

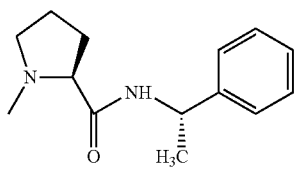
Xbl
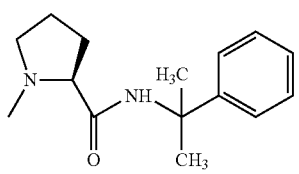
Xbm
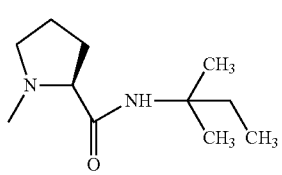
Xbn
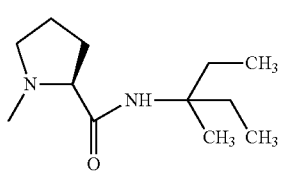
Xbo
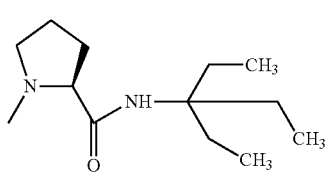
Xbp
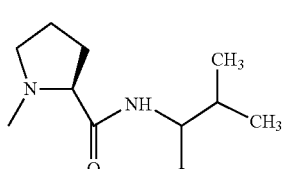
Xbq
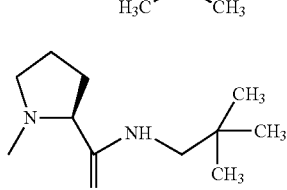
Xbr
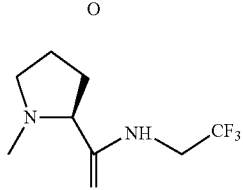
Xbs
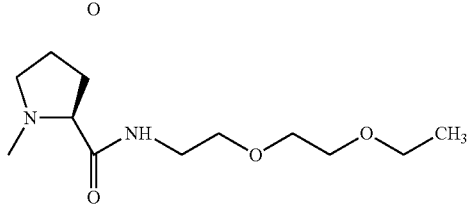
Xbt
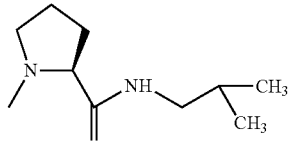
Xbu
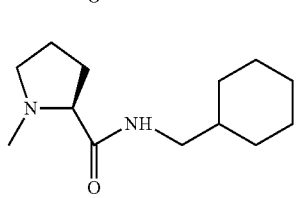
Xbv
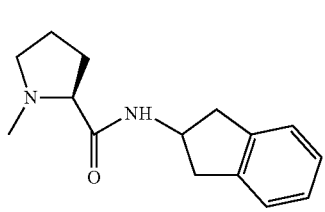
Xbw
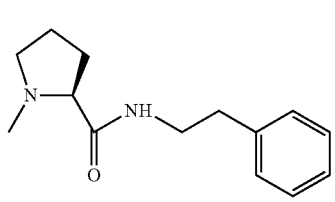
Xbx
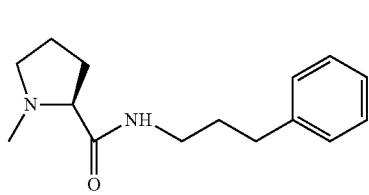
Xby
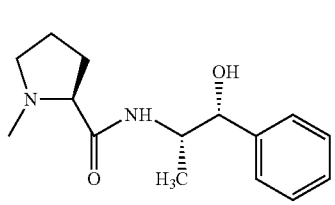
Xbz
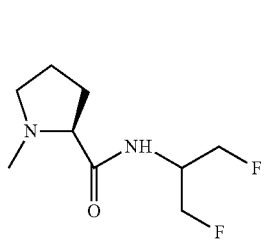
Xca
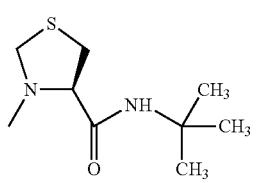
Xcb Proline adamantyl (1) amide
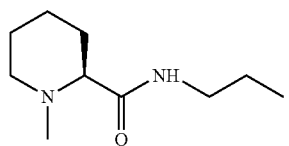
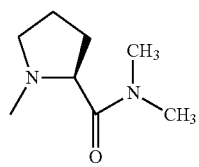
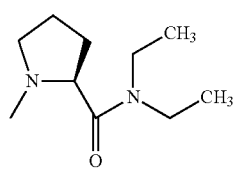
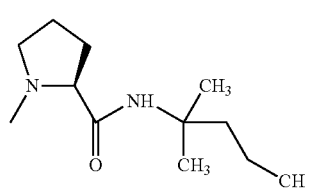
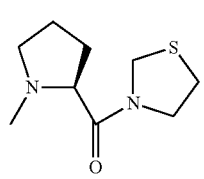
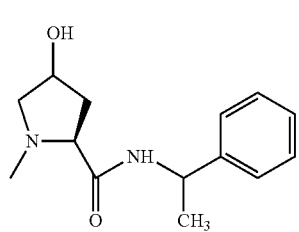
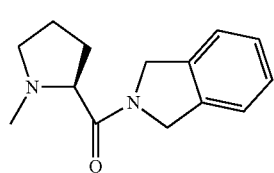
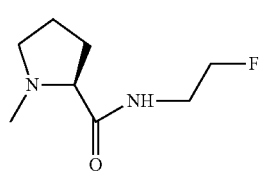
Xcc
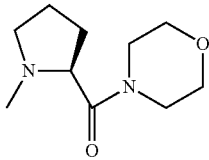
Xcd
Xce
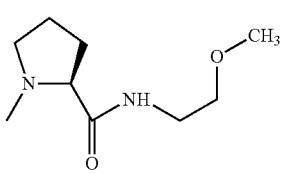
Xcf
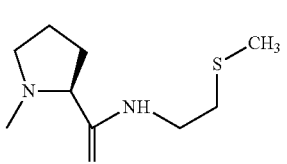
Xcg
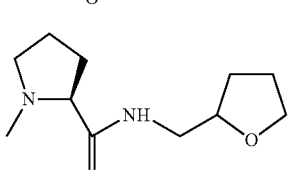
Xch
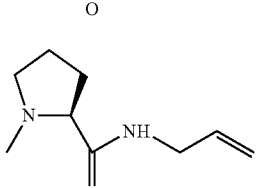
Xci
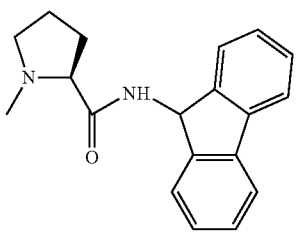
Xcj
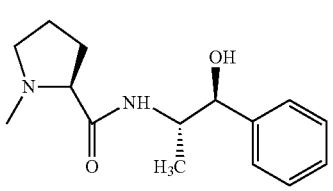
Xck
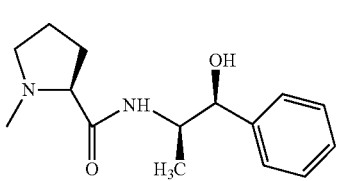
Xcl
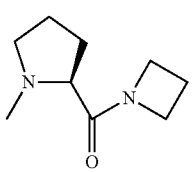
Xcm
Xcn
Xco
Xcp
Xcq
Xcr
Xcs
Xct
Xcu

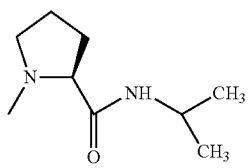
N-Methyl-N-ethyl-valine
N,N-Diethylvaline
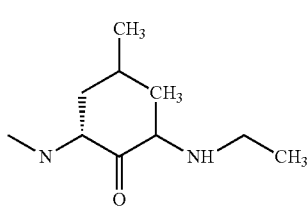
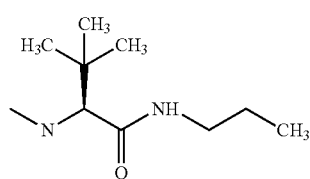
N-Methyl-2-aminobutyroyl
2-aminobutyroyl
N,N-Dimethyl-2-aminobutyroyl
N,N-Dimethyl-2-tert·butylglycine
N,N-Dimethyl-isoleucine
2-tert·butylglycine
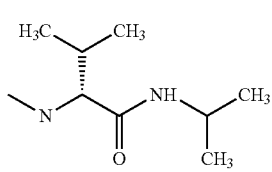
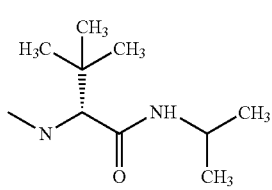
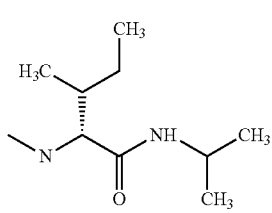
Xcv
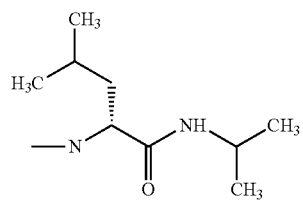
Xcw
Xcx  N-Methyl-2-tert·butylglycine
Xcy
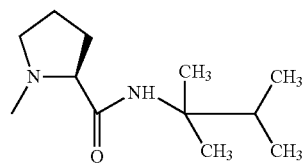
Xcz
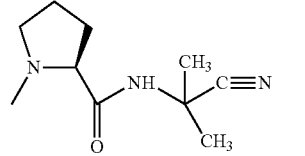
Xda
Xdb
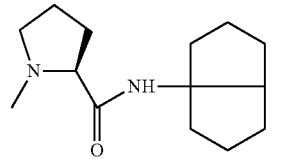
Xdc
Xdd
Xde  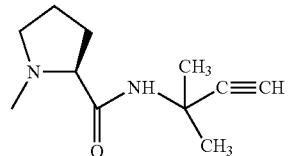
Xdf
Xdg
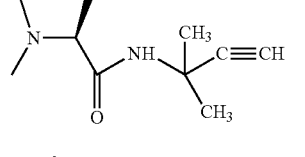
Xdh
Xdi
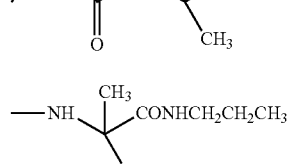
Xdk
Xdl
Xdm
Xdn
Xdo
Xdp
Xdq
Xdr
Xds
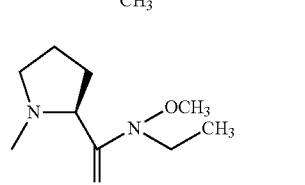
Xdt
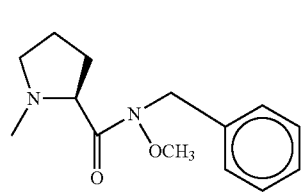

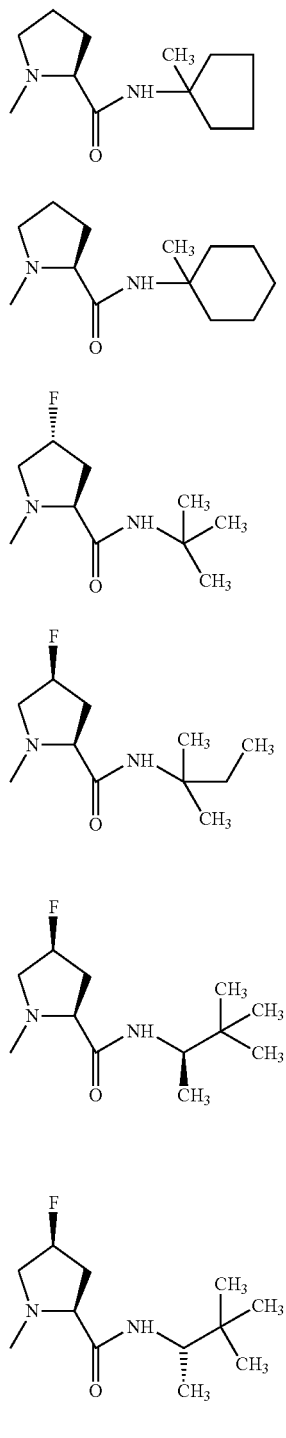
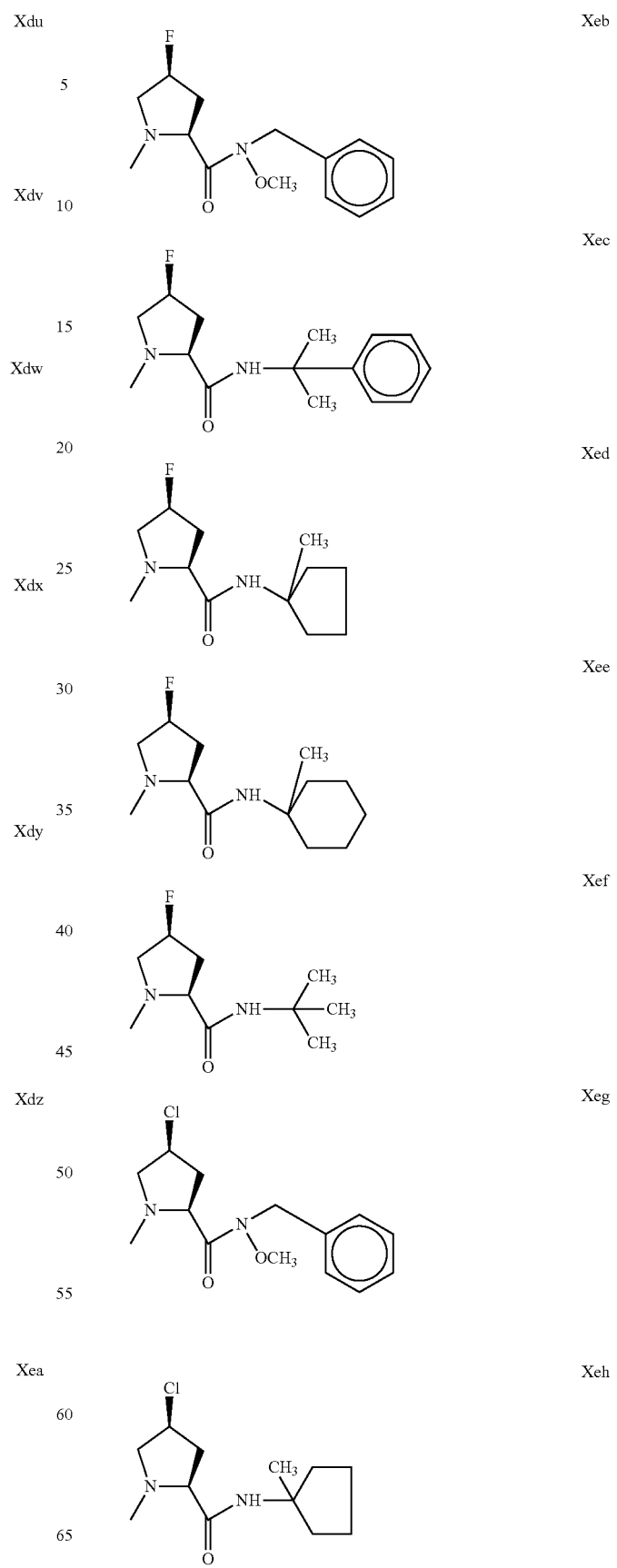

-continued

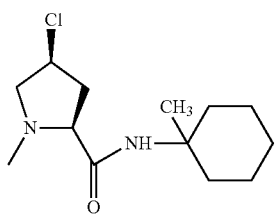

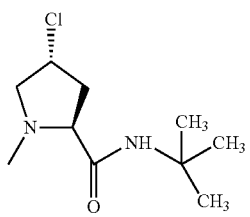

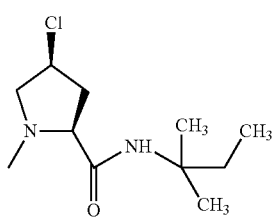

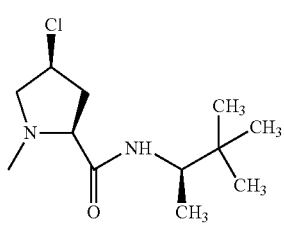

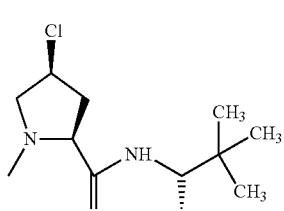

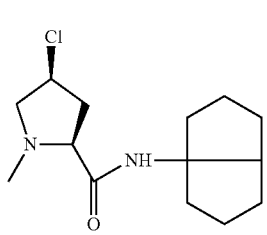

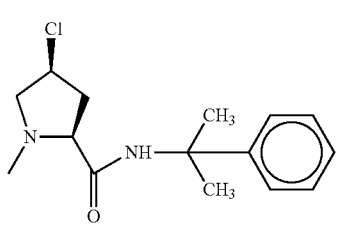

-continued

Xei

Xek

Xel

Xem

Xen

Xeo

Xep

Xeq

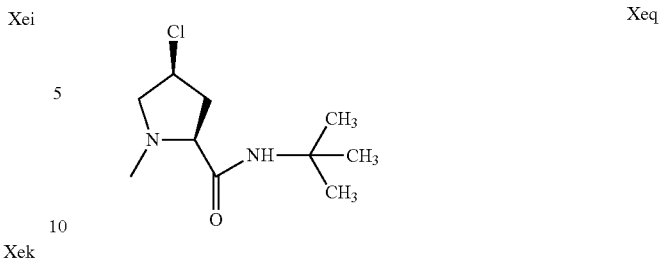

Compounds of this invention may be assayed for anti-cancer activity by conventional methods, including for example, the methods described below.

A. In Vitro Methodology

Cytotoxicity was measured using a standard methodology for adherent cell lines such as the microculture tetrazolium assay (MTT). Details of this assay have been published (Alley, M C et al, Cancer Research 48:589-601, 1988). Exponentially growing cultures of tumor cells such as the HT-29 colon carcinoma or LX-1 lung tumor are used to make microtiter plate cultures. Cells are seeded at 3000 cells per well in 96-well plates (in 150.mu.l or media), and grown overnight at 37° C. Test compounds are added, in 10-fold dilutions [varying from $10^{0.4}$ M to $10^{0.10}$ M. Cells are then incubated for 72 hours. To determine the number of viable cells in each well, the MTT dye is added (50 μl or 3 mg/ml solution of 3-(4,5-dimethylthiazol-2-yl)-2,5-diphenyltetrazolium bromide in saline). This mixture is incubated at 37° C. for 5 hours, and then 50 μl of 25% SDS, pH2 is added to each well. After an overnight incubation, the absorbance of each well at 550 nm is read using an ELISA reader. The values for the mean+/−SD of data from replicated wells are calculated, using the formula % T/C (% viable cells treated/control).

$$\frac{OD \text{ of treated cells}}{OD \text{ of control cells}} \times 100 + \% \ T/C$$

The concentration of test compound which gives a T/C of 50% growth inhibition was designated as the $IC_{50}$ value.

B. In Vivo Methodology

Compounds of this invention were further tested in preclinical assay for in vivo activity which is indicative of clinical utility. Such assays were conducted with nude mice into which tumor tissue, preferably of human origin, had been transplanted (xenografted), as is well known in this field. Test compounds were evaluated for their anti-tumor efficacy following administration to the xenograft-bearing mice.

More specifically, human breast tumors (MX-1) which had been grown in athymic nude mice were transplanted into new recipient mice, using tumor fragments which were about 50 mg in size. The day of transplantation was designated as day 0. Six to ten days later, mice were treated with the test compounds given as an intravenous injection or orally, in groups of 5-10 mice at each dose. Compounds were given every other day, for 3 weeks, at doses from 1-200 mg/kg body weight.

Tumor diameters and body weights were measured twice weekly. Tumor volumes were calculated using the diameters measured with Vernier calipers, and the formula (Length×width$^2$)/2=mm$^3$ of tumor volume Mean tumor volumes are calculated for each treatment group, and T/C values determined for each group relative to the untreated control tumors.

The new compounds possess good tumor inhibiting properties.

The invention claimed is:

1. A method of treating a solid tumor in a mammal, comprising administering to the mammal an effective amount of a peptide, wherein the peptide is of the formula I:

$$\text{Me}_2\text{Val-Val-MeVal-Pro-Pto-NHC}(\text{CH}_3)_3 \quad \text{(SEQ ID NO: 1)} \quad \text{(I)}$$

or a pharmaceutically acceptable salt thereof.

2. The method of claim 1 wherein the pharmaceutically acceptable salt is a hydrochloride salt.

3. The method of claim 1, wherein the solid tumor is a tumor of the lung, breast, colon, prostate, bladder, rectum, or an endometrial tumor.

4. The method of claim 1, wherein the peptide is of formula I is orally or parenterally administered to the mammal.

5. The method of claim 1, wherein the peptide is of formula I is subcutaneously, intravenously, intramuscularly or intraperitoneally administered to the mammal.

6. The method of claim 4, wherein the peptide is of formula I is orally administered at a dose of about 0.05 to 50 milligrams per kilogram of body weight.

7. The method of claim 4, wherein the peptide of formula I is parenterally administered at a dose of about 0.01 to 20 milligrams per kilogram of body weight.

8. The method of claim 1, wherein the peptide of formula I is in the in the form of a pharmaceutical composition.

9. The method of claim 1, wherein the mammal is human.

10. A method of treating a hematological malignancy in a mammal, comprising administering to the mammal an effective amount of a peptide, wherein the peptide is of the formula I:

$$\text{Me}_2\text{Val-Val-MeVal-Pro-Pro-NHC}(\text{CH}_3)_3 \quad \text{(SEQ ID NO: 1)} \quad \text{(I)}$$

or a pharmaceutically acceptable salt thereof.

11. The method of claim 10 wherein the pharmaceutically acceptable salt is a hydrochloride salt.

12. The method of claim 10, wherein the hematological malignancy is a leukemia or a lymphoma.

13. The method of claim 10, wherein the peptide of formula I is orally or parenterally administered to the mammal.

14. The method of claim 10, wherein the peptide of formula I is subcutaneously, intravenously, intramusculary or intraperitoneally administered to the mammal.

15. The method of claim 13, wherein the peptide of formula I is orally administered at a dose of about 0.05 to 50 milligrams per kilogram of body weight.

16. The method of claim 13, wherein the peptide of formula I is parenterally administered at a dose of about 0.01 to 20 milligrams per kilogram of body weight.

17. The method of claim 10 wherein the peptide of formula I is in the in the form of a pharmaceutical composition.

18. The method of claim 10, wherein the mammal is human.

* * * * *